United States Patent [19]

Guerry et al.

[11] Patent Number: 5,106,878
[45] Date of Patent: Apr. 21, 1992

[54] USE OF SUBSTITUTED AMINOALKOXYBENZENE DERIVATIVES IN THE CONTROL OR PREVENTION OF FUNGAL INFECTIONS

[75] Inventors: Philippe Guerry, Basel; Synèse Jolidon, Birsfelden; René Zurflüh, Bülach, all of Switzerland

[73] Assignee: Hoffmann-La Roche Inc., Nutley, N.J.

[21] Appl. No.: 556,241

[22] Filed: Jul. 20, 1990

[30] Foreign Application Priority Data

Jul. 27, 1989 [CH] Switzerland .................. 2798/89
May 8, 1990 [CH] Switzerland .................. 1553/90

[51] Int. Cl.$^5$ ..................................... H61K 31/135
[52] U.S. Cl. ................................. 514/651; 514/524; 514/648
[58] Field of Search .............. 564/353, 324; 514/651, 514/524, 648; 558/415, 422

[56] References Cited

U.S. PATENT DOCUMENTS

| | | | |
|---|---|---|---|
| 1,894,865 | 1/1933 | Hartmann et al. | 564/354 |
| 2,668,813 | 2/1954 | Goldberg et al. | 546/232 |
| 2,668,850 | 2/1954 | Goldberg et al. | 52/3 |
| 2,771,393 | 11/1956 | Libermann et al. | 514/651 |
| 2,796,435 | 6/1957 | Goldberg | 564/354 |
| 3,123,643 | 3/1964 | Palopoli et al. | 564/323 |
| 3,312,696 | 4/1967 | Turbanti | 544/174 |
| 3,553,332 | 1/1971 | Grunberg | 514/651 |
| 3,560,567 | 2/1971 | Ruegg et al. | 564/324 |
| 3,864,501 | 2/1975 | Yokoyama et al. | 426/268 |
| 4,732,896 | 3/1988 | Bourgery et al. | 564/353 |

FOREIGN PATENT DOCUMENTS

| | | | |
|---|---|---|---|
| 114410 | 12/1982 | European Pat. Off. | |
| 115080 | 12/1982 | European Pat. Off. | |
| 2616484 | 10/1977 | Fed. Rep. of Germany | 514/651 |
| 3233828 | 3/1984 | Fed. Rep. of Germany | 564/353 |

OTHER PUBLICATIONS

Chem. Abst., 52, 440a, (1959), (corresponds to Document AA).
Chem. Abst., 63, 6907f, (1965).
Antimicrobial Agents and Chemotherapy, Jul., 1981, pp. 71-74.
Arzneim.-Forsch./Drug Res., 34(I), No. 2, 1984, pp. 139-146.
Pesticide Biochemistry and Physiology, 25, 1986, pp. 112-124.

*Primary Examiner*—Richard L. Raymond
*Attorney, Agent, or Firm*—George M. Gould; George W. Johnston; Alan P. Kass

[57] ABSTRACT

The compound of the formula

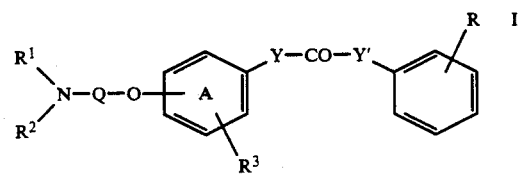

wherein each of $R^1$ and $R^2$ individually is hydrogen, lower alkyl or lower alkenyl or together signify straight-chain alkylene with 2 or 4 carbon atoms, $R^3$ is hydrogen, halogen or lower alkyl, Q is alkylene with 4 to 11 carbon atoms and at least 4 carbon atoms between the two free valencies or alkenylene with 4 to 11 carbon atoms and at least 4 carbon atoms between the two free valencies and each of Y and Y' individually is a direct bond or the group —CH$_2$—, —CH$_2$CH$_2$—, —CH=CH— or —C≡C—, the group $R^1R^2N$—Q—O— is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy, and their pharmaceutically acceptable acid addition salts can be used for the control or prevention of fungal infections, especially of topical or systemic infections which are caused by pathogenic fungi, and for the manufacture of antifungally-active medicaments. The compounds of formula I have not only a pronounced antifungal activity, but they also exhibit synergistic effects in combination with other known antifungally-active substances which inhibit sterol biosynthesis such as ketoconazole and terbinafine.

5 Claims, No Drawings

USE OF SUBSTITUTED AMINOALKOXYBENZENE DERIVATIVES IN THE CONTROL OR PREVENTION OF FUNGAL INFECTIONS

BACKGROUND OF THE INVENTION

1. Field of the Invention

The invention relates to substituted aminoalkoxybenzene derivatives and their pharmaceutically acceptable acid addition salts for the control of or prevention of fungal infections.

SUMMARY OF THE INVENTION

The present invention is concerned with compounds having the formula

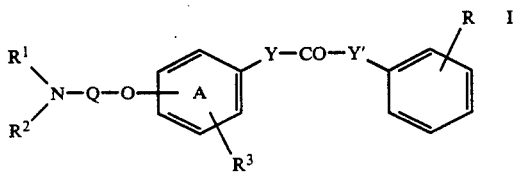

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 4 to 11 carbon atoms and at least 4 carbon atoms between the two free valencies or alkenylene with 4 to 11 carbon atoms and at least 4 carbon atoms between the two free valencies and each of Y and Y' individually is a direct bond or the group —$CH_2$—, —$CH_2CH_2$—, —CH=CH— or —C≡C—, the group $R^1R^2N$—Q—O— is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy, and of their pharmaceutically acceptable acid addition salts. These compounds are useful for the control of or prevention of fungal infections, especially of topical or systemic infections which are caused by pathogenic fungi.

The compounds of formula I have not only a pronounced antifungal activity, but they also exhibit synergistic effects in combination with other known antifungally-active substances which inhibit sterol biosynthesis such as ketoconazole and terbinafine. The compounds of formula I can accordingly be used as medicaments, especially for the control of or prevention of topical or systemic infections which are caused by pathogenic fungi in mammals, humans and non-humans.

DETAILED DESCRIPTION OF THE INVENTION

The present invention is concerned with compounds having the formula

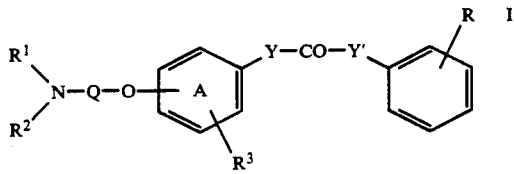

wherein each of $R^1$ and $R^2$ individually is hydrogen, lower alkyl or lower alkenyl or together are straight-chain alkylene with 2 to 4 carbon atoms. R is hydrogen, halogen or lower alkyl, Q is alkylene with 4 to 11 carbon atoms and at least 4 carbon atoms between the two free valencies or alkenylene with 4 to 11 carbon atoms and at least 4 carbon atoms between the two free valencies or alkenylene with 4 to 11 carbon atoms and at least 4 carbon atoms between the two free valencies and each of Y and Y' individually is a direct bond or the group —$CH_2$—, —$CH_2CH_2$—, —CH=CH— or —C≡C—, the group $R^1R^2N$—Q—O— is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy, and of their pharmaceutically acceptable acid addition salts. The compounds are used to control or prevent fungal infections, especially topical or systemic infections which are caused by pathogenic fungi. The compounds also are used to produce antifungally-active medicaments.

The compounds of formula I have not only a pronounced antifungal activity, but they also exhibit synergistic effects in combination with other known antifungally-active substances which inhibit sterol biosynthesis such as ketoconazole and terbinafine. The compounds of formula I can accordingly be used as medicaments, especially for the control of or prevention of topical or systemic infections which are caused by pathogenic fungi in mammals, humans and non-humans.

Suitable sterol biosynthesis inhibitors for combination with compounds of formula I are, for example, systemic antifungally-active azoles and systemic antifungally-active allylamines.

Examples of the antifungally-active azoles include bifonazole, butoconazole, cloconazole, clotrimazole, econazole, enilconazole, fenticonazole, isoconazole, ketoconazole, miconazole omoconazole, oxiconazole, sulconazole, tioconazole fluconazole, itraconazole, terconazole and the like. Examples of the antifungally-active allylamines include naftifine, terbinafine and the like.

In a special embodiment, the present invention is concerned with the use of 4-[(4-(dimethylamino)butyl)oxy]-benzophenone for the control of or prevention of fungal infections.

Further objects of the present invention are compounds having the formula

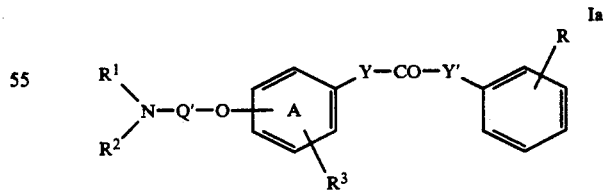

wherein Q' is alkylene with 5 to 11 carbon atoms and at least 5 carbon atoms between the two free valencies or alkenylene with 4 to 11 carbon atoms and at least 4 carbon atoms between the two free valencies and $R^1$, $R^2$, $R^3$, R, A, Y and Y' are as defined above, and their pharmaceutically acceptable acid addition salts for use as therapeutically active substances, especially as antifungally-active substances, corresponding medicaments based on these compounds of formula Ia. Compounds of formula Ia and their intermediates are also objects of the present invention, insofar as each of Y and Y' do not simultaneously represent a direct bond when Q' is alkylene with 5 carbon atoms and each of $R^1$ and $R^2$ simultaneously represent lower alkyl with more than 2 carbon atoms.

Compounds of formula I in which Q is unbranched alkylene with 4 carbon atoms belong to a class of substance which is known. Such compounds are described in U.S. Pat. No. 3,864,501 as agents for improving the coloring of fruits and vegetables. Such compounds are described in U.S. Pat. No. 3,312,696 as coronary dilators. Such compounds are described in European patent publication No. 115,080 as intermediates for the production of active substances against alcohol poisonings.

Compounds of formula I where each of Y and Y' individually is a direct bond, each of $R^1$ and $R^2$ individually is lower alkyl with more than 2 carbon atoms and Q is unbranched alkylene with 5 carbon atoms also belong to a class of substance which is known. Such compounds are described in European Patent Publication No. 114.410 as intermediates for the manufacture of active substances against alcohol poisonings.

The term "lower" denotes residues and compounds having a maximum of seven, preferably a maximum of four, carbon atoms. The term "alkyl" denotes straight-chain or branched, saturated hydrocarbon residues such as methyl, ethyl, propyl, isopropyl and t-butyl. The term "alkenyl" denotes straight-chain or branched hydrocarbon residues having an olefinic double bond, such as allyl and 2-butenyl. The term "alkoxy" denotes alkyl groups attached via an oxygen atom, such as methoxy and ethoxy. The term "alkylene" denotes straight-chain or branched, saturated hydrocarbon residues having two free valencies, such as dimethylene, trimethylene or tetramethylene. The term "alkenylene" denotes straight-chain or branched hydrocarbon residues having at least one olefinic double bond and two free valencies, such as 2-butene-1,4-diyl. The term "halogen" denotes fluorine, chlorine, bromine and iodine.

The term "leaving group" represents conventional leaving groups typically used in the art. Preferably, the leaving groups are halogen atoms, especially chlorine, bromine and iodine, and lower alkylsulphonyloxy and arylsulphonyloxy groups such as methylsulphonyloxy, benzenesulphonyloxy, p-toluenesulphonyloxy and p-chlorobenzenesulphonyloxy. The term "aryl" represents in the scope of the present invention phenyl which is unsubstituted or substituted with at least one of halogen, lower alkyl or lower alkoxy.

As discussed herein, positions 3 and 4 of ring A are shown below:

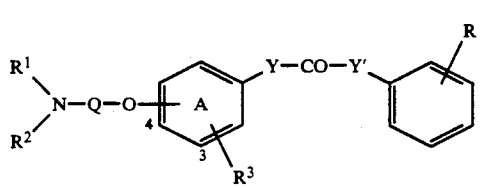

I

Preferably, each of $R^1$ and $R^2$ individually is $C_{1-4}$-alkyl or $C_{3-4}$-alkenyl or together are $C_{3-4}$-alkylene. Q' preferably is unbranched alkylene with 5 to 7 carbon atoms. The group $R^1R^2N-Q'-O-$ is preferably attached to the 4-position of ring A. Y preferably is a direct bond or the group $-CH_2-$, especially a direct bond. Y' preferably is a direct bond or the group $-CH_2-$, $-CH_2CH_2-$ or $-CH=CH-$, especially a direct bond or the group $-CH_2-$. The symbol R preferably designates that the ring to which it is attached is unsubstituted or is substituted, preferably mono- or disubstituted, by halogen, nitro and/or lower alkyl.

Especially preferred novel compounds of formula Ia in the scope of the present invention are:
4-[(6-(dimethylamino)hexyl)oxy]-2-phenylacetophenone,
4-[(6-(dimethylamino)hexyl)oxy]benzophenone,
4'-[(6-(diethylamino)hexyl)oxy]-3-phenylpropiophenone,
4'-[(6-(dimethylamino)hexyl)oxy]-3-phenylpropiophenone.
(E)-4'-[[6-(dimethylamino)hexyl]oxy]-3-phenylacrylophenone,
4-[(6-(dimethylamino)hexyl)oxy]-4'-fluorobenzophenone,
4-[(6-(1-azetidinyl)hexyl)oxy]benzophenone.
4-[(6-(1-pyrrolidinyl)hexyl)oxy]benzophenone,
2-[4-[[6-(dimethylamino)hexyl]oxy]phenyl]acetophenone,
4-[(7-(dimethylamino)heptyl)oxy]benzophenone,
4-[(5-(dimethylamino)pentyl)oxy]benzophenone,
4-[(6-(allylmethylamino)hexyl]oxy]-2-phenylacetophenone,
4-[[6-(allylmethylamino)hexyl]oxy]-4'-fluorobenzophenone,
trans-4-[[4-(allylmethylamino)-2-butenyl]oxy]benzophenone,
4-[[6-(allylmethylamino)hexyl]oxy]-3-methylbenzophenone,
4-[[6-(allylmethylamino)hexyl]oxy]-4'-nitrobenzophenone and
4-[[6-(allylmethylamino)hexyl]oxy]-3-chlorobenzophenone.

The novel compounds of formula Ia and their pharmaceutically acceptable acid addition salts can be manufactured in accordance with the invention by
a) reacting a compound having the formula

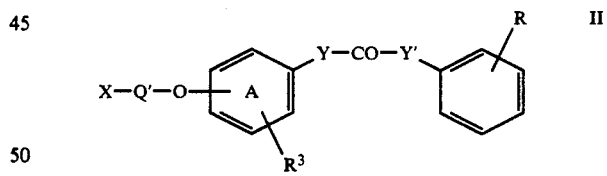

II wherein X is a leaving group and A, Q', Y, Y', $R^3$ and R are defined above, with an amine having the formula $HNR^1R^2$, wherein $R^1$ and $R^2$ are defined above, or b) oxidizing a compound having the formula

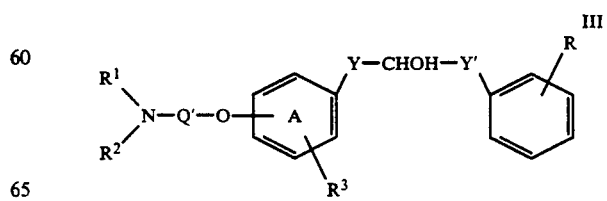

III wherein A, $R^1$, $R^2$, Q', Y, Y', $R^3$ and R are defined above, or
c) reacting a compound having the formula

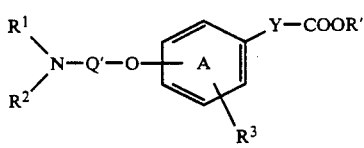

wherein R' is lower alkyl and A, R$^1$, R$^2$,
R$^3$, Q' and Y are defined above,
with a compound having the formula

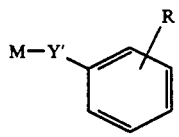

wherein M is —MgCl, —MgBr, —MgI or —Li and Y'
and R are defined above,
d) reacting a compound having the formula

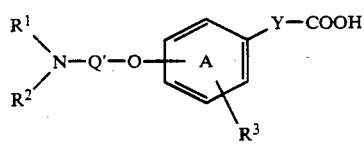

wherein A, R$^1$, R$^2$, R$^3$, Q' and Y are defined above,
in the form of a reactive derivative in the presence of a Lewis acid with a compound having the formula

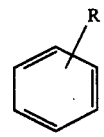

wherein R is defined above, or
e) reacting a compound having the formula

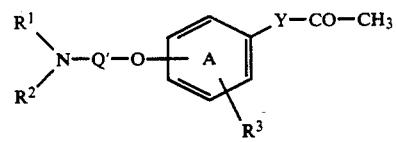

wherein A, R$^1$, R$^2$, R$^3$, Q' and Y are defined above,
in the presence of a base with a compound having the formula

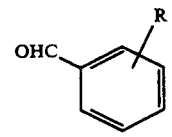

wherein R is defined above,
or
f) hydrogenating a compound having the formula

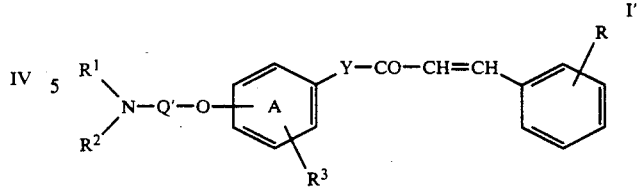

wherein A, R$^1$, R$^2$, R$^3$, Q', Y and R are defined above,
or
g) reacting a compound having the formula

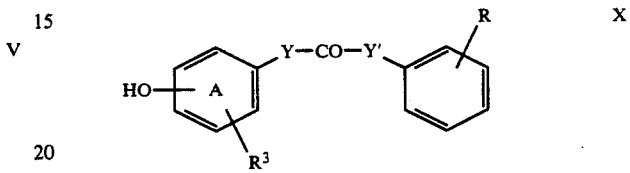

wherein A, R, R$^3$, Y and Y' are defined above, in the presence of triphenylphosphine and a di(lower alkyl) azodicarboxylate with a compound having the formula

R$^1$R$^2$N—Q'—OH    XI wherein R$^1$, R$^2$ and Q' are defined above, and
h) if desired, converting a compound of formula Ia obtained into a pharmaceutically acceptable acid addition salt.

The reaction of a compound of formula II with an amine of the formula HNR$^1$R$^2$ in accordance with process variant a) can be carried out according to methods which are known to any person skilled in the art. The reaction is preferably carried out in a polar solvent and in the presence of a base as the acid-binding agent in a temperature range of about 0° C. to about 150° C. Suitable solvents are, for example, lower alcohols such as methanol and ethanol and lower dialkyl ketones such as acetone. Suitable bases are, for example, excess amine of the formula HNR$^1$R$^2$, tertiary amines such as triethylamine and inorganic bases such as alkali metal carbonates, alkali metal hydroxides and alkali metal alcoholates.

The oxidation of a compound of formula III in accordance with process variant b) can be carried out according to methods which are known to any person skilled in the art. The reaction is preferably carried out in an inert solvent and in the presence of an oxidation agent in a temperature range of about −80° C. to about room temperature (about 20° C.). Suitable solvents are, for example, chlorinated lower hydrocarbons such as methylene chloride and chloroform. Suitable oxidation agents are, for example, manganese dioxide or mixtures of dimethyl sulphoxide with oxalyl chloride, dicyclohexylcarbodiimide or acetic anhydride and a tertiary amine such as triethylamine.

The reaction of a compound of formula IV with a compound of formula V in accordance with process variant c) can be carried out according to methods which are known to any person skilled in the art. The reaction is preferably carried out in an inert solvent and in a temperature range of about −80° C. to about room temperature (about 20° C.). Suitable solvents are, for example, open-chain and cyclic ethers such as diethyl ether, methyl t-butyl ether and tetrahydrofuran and mixtures thereof.

The reaction of a reactive derivative of a compound of formula VI with a compound of formula VII in accordance with process variant d) can be carried out according to methods which are known to any person skilled in the art. The reaction is preferably carried out in an inert solvent and in the presence of a Lewis acid in a temperature range of about 0° C. to about 100° C. Suitable solvents are, for example, halogenated lower hydrocarbons such as methylene chloride, chloroform and ethylene chloride, nitrobenzene, carbon disulphide and excess compound of formula VII. Aluminium chloride is preferably used as the Lewis acid. Suitable reactive derivatives of compounds of formula VI are, for example, the corresponding carboxylic acid chlorides.

The reaction of a compound of formula VIII with a compound of formula IX in the presence of a base in accordance with process variant e) can be carried out according to methods which are known to any person skilled in the art. The reaction is preferably carried out in a polar solvent and in a temperature range of about 0° C. to about 60° C. Suitable solvents are, for example, lower alcohols such as methanol and ethanol and mixtures thereof with water. Alkali metal carbonates and alkali metal hydroxides such as potassium carbonate and sodium hydroxide are preferably used as the bases.

The hydrogenation of a compound of formula I' in accordance with process variant f) can be carried out according to methods which are known to any person skilled in the art. The reaction is preferably carried out in a polar solvent using elemental hydrogen in the presence of a suitable hydrogenation catalyst and in a temperature range of about 0° C. to about room temperature (about 20° C.). Suitable solvents are, for example, lower alcohols such as methanol and ethanol. Suitable catalysts are, for example, palladium or platinum on carbon, platinum oxide or Raney-nickel.

The reaction of a compound of formula X with a compound of formula XI in accordance with process variant g) is also a method which is known in the art as the so-called Mitsunobu coupling. It is preferably carried out in an inert organic solvent and in a temperature range of about 0° C. up to the boiling temperature of the reaction mixture, which can easily be ascertained by those of ordinary skill in the art. Suitable solvents are, for example, chlorinated lower hydrocarbons such as methylene chloride and chloroform and open-chain and cyclic ethers such as diethyl ether, methyl t-butyl ether and tetrahydrofuran and mixtures thereof.

The manufacture of pharmaceutically acceptable acid addition salts of compounds of formula Ia in accordance with process variant h) can be carried out according to methods which are known to any person skilled in the art. Salts with pharmaceutically acceptable inorganic and organic acids come into consideration. The hydrochlorides, hydrobromides, sulphates, nitrates, citrates, acetates, succinates, fumarates, methanesulphonates and the p-toluenesulphonates are preferred acid addition salts.

The known compounds of formula I and their pharmaceutically acceptable acid addition salts can also be manufactured according to processes a)-h) above. The corresponding starting materials can be prepared as described hereinafter for the starting materials for the novel compounds of formula Ia.

The compounds of formulae II. III, IV. VI and VIII which are used as starting materials are novel and also form objects of the present invention. They can be prepared, for example, in accordance with the following Reaction Schemes I-IV and the following descriptions of the various reactions. The remaining compounds which are used as starting materials belong to classes of substances which are known. In these Reaction Schemes, $R^1$, $R^2$, $R^3$, R, R', A, M, Q', X, Y and Y' are defined above for the novel compounds of formula Ia or for their manufacture.

Reaction Scheme I

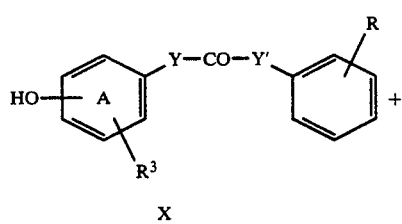

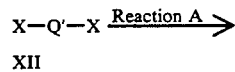

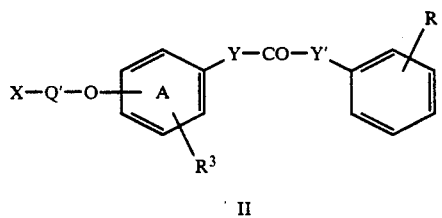

Reaction Scheme II

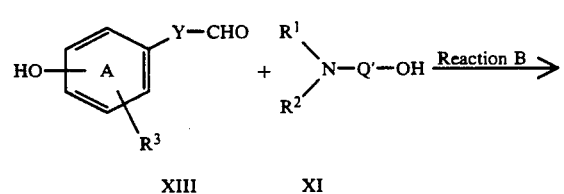

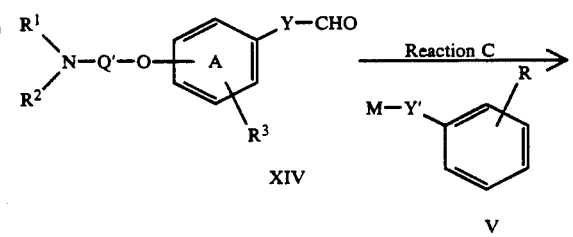

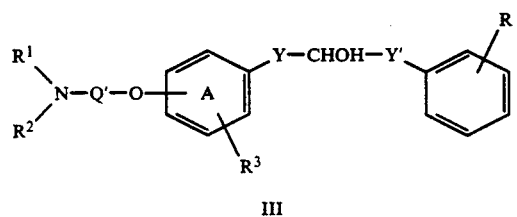

Reaction Scheme III

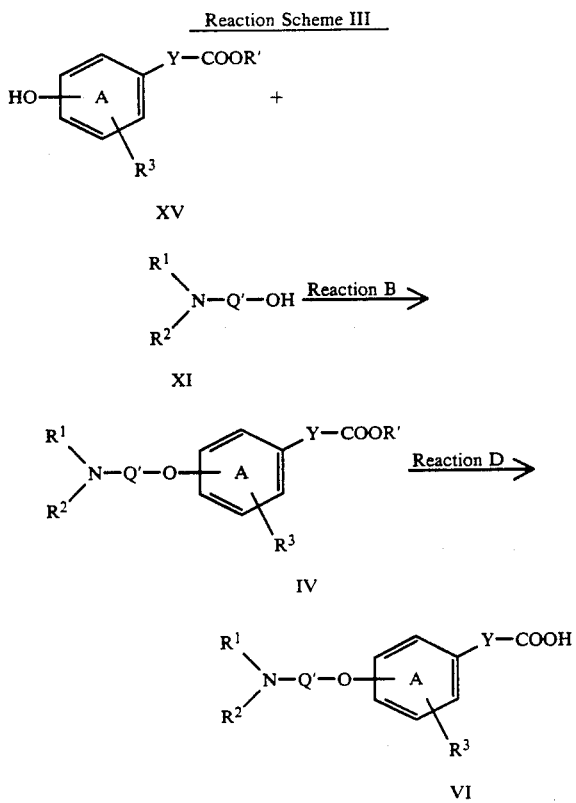

Reaction Scheme IV

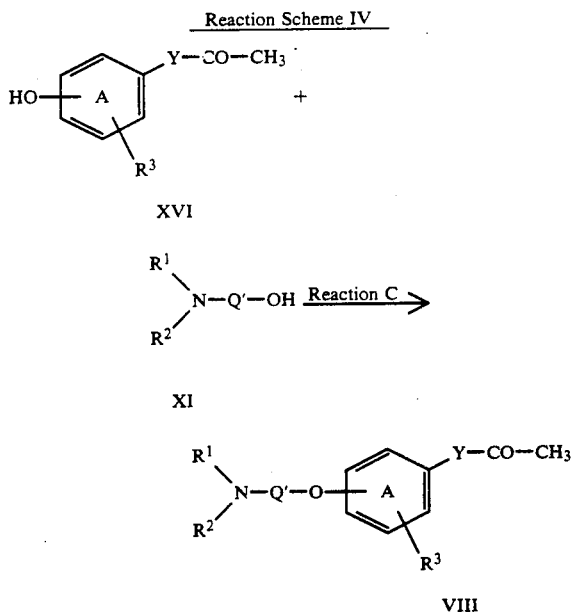

Reaction A

This reaction can be carried out according to methods which are known to any person skilled in the art and is preferably carried out in a polar solvent and in the presence of a base in a temperature range of about 0° C. to about 150° C. Suitable solvents are, for example, lower alcohols such as methanol and ethanol and lower dialkyl ketones such as acetone. Suitable bases are, for example, alkali metal carbonates, alkali metal hydroxides, alkali metal alcoholates and alkali metal hydrides.

Reaction A can, however, also be carried out in a two-phase system in the presence of a phase transfer catalyst, for example a quaternary ammonium salt. Preferably, an aqueous alkali such as sodium hydroxide solution is used as the aqueous phase and a halogenated lower hydrocarbon such as methylene chloride or an aromatic hydrocarbon such as toluene is used as the organic phase. The compound of formula XII is preferably used in excess, with 2 to 4 mol equivalents of the compound of formula XII preferably being used.

Reaction B

This reaction is the so-called Mitsunobu coupling described above in connection with process variant g). It is preferably carried out in an inert organic solvent and in a temperature range of about 0° C. up to the boiling temperature of the reaction mixture. Suitable solvents are, for example, chlorinated lower hydrocarbons such as methylene chloride and chloroform and open-chain and cyclic ethers such as diethyl ether, methyl t-butyl ether and tetrahydrofuran and mixtures thereof.

Reaction C

The reaction of a compound of formula XIV with a compound of formula V can be carried out according to methods which are known to any person skilled in the art. The reaction is preferably carried out in an inert solvent and in a temperature range of about −80° C. to about room temperature (about 20° C.). Suitable solvents are, for example, open-chain and cyclic ethers such as diethyl ether, methyl t-butyl ether and tetrahydrofuran and mixtures thereof.

Reaction D

This reaction is a hydrolysis. This can be carried out according to methods which are known to any person skilled in the art and is preferably carried out by treatment with an alkali metal hydroxide such as sodium hydroxide and potassium hydroxide or with a mineral acid such as hydrochloric acid and hydrobromic acid in a polar solvent and in a temperature range of about 0° C. to about 100° C. Suitable solvents are, for example, mixtures of lower alcohols such as methanol and ethanol and water-miscible open-chain and cyclic ethers such as tetrahydrofuran with water.

As already mentioned, the compounds of formula I and their pharmaceutically acceptable acid addition salts have valuable antifungal properties. They are active against a large number of pathogenic fungi which cause topical and systemic infections, such as Candida albicans and Histoplasma capsulatum, 2,3-Expoxysqualene-lanosterol cyclase, an enzyme involved in the sterol biosynthesis of eucaryotic cells, is an essential enzyme for the fungi. Thus, for example, a S. cerevisiae strain in which this enzyme is absent is not viable [F. Karst & F. Lacroute, Molec. Gen. Genet. 154, 269 (1977)]. The inhibitory activity of the compounds of formula I on the above-mentioned enzyme from C. albicans was taken as the measurement for the antifungal activity. The inhibition can be measured, for example, by means of the method described hereinafter.

Determination of the IC50 value for the inhibition of 2,3-epoxysqualene-lanosterol cyclase from *Candida albicans*

The cells of a culture of Candida albicans are collected at the end of the logarithmic growth phase and washed with 100 mM phosphate buffer (pH=6.9), digestion buffer and 50 mM phosphate buffer (pH=7.4) containing 1M mannitol and 5 mM DTT.

1.0 g of these cells is suspended in 5 ml of digestion buffer, treated with 1 mg of Zymolase 100T (Seikagaku Kogyo, Japan) and 12.5 µl of β-mercaptoethanol and incubated at 30° C. for 30 minutes. The resulting protoplasts are isolated by centrifugation (10 minutes at 2500 g) and subsequently ruptured by the addition of 2 ml of 100 mM phosphate buffer (pH=6.9) By renewed centrifugation (10 minutes at 10000 g) there is obtained a cell-free extract (CFE) as the supernatant. This is diluted to 10 mg of protein per ml and the pH is brought to 6.9.

The activity of the 2,3-epoxysqualene-lanosterol cyclase in the CFE is measured by reacting $^{14}$C-squalene epoxide in the presence of n-decylpentaoxyethylene as a detergent. Titration with measured amounts of the test substance permits the determination of the IC$_{50}$ value (concentration of test substance which reduces the enzyme activity by half).

The test is carried out as follows:

A 250 µM solution of $^{14}$C-squalene epoxide in 100 mM phosphate buffer (pH=6.9) with the addition of 1% n-decylpentaoxyethylene is prepared by ultrasonic treatment. 100 µl of this solution is treated with 20 µl of a solution of the test substance in dimethyl sulphoxide (or 20 µl of pure dimethyl sulphoxide as the control). After the addition of 880 µl of CFE the well-mixed solution is incubated at 30° for 1 hour while shaking. Subsequently, the reaction is stopped by the addition of 500 µl of 15 percent potassium hydroxide in 90 percent ethanol.

The mixture is extracted twice with 1 ml of n-hexane, the hexane is evaporated and the lipid residue is taken up in 200 µl of diethyl ether. After thin-layer chromatography on silica gel using methylene chloride as the eluent the plates are investigated using a radioactive thin-layer scanner.

Only lanosterol is found as the radioactive product under the conditions used. Its amount is compared with the amount of radioactive lanosterol in the control.

The IC$_{50}$ values are determined graphically and are given in µg of test substance per ml. Table I contains IC$_{50}$ values determined in the above test for representative members of the class of compound defined by formula I as well as data concerning the acute toxicity in the case of subcutaneous administration to mice (LD$_{50}$ in mg/kg).

TABLE I

Structure:
$R^1R^2N-Q-O-$[phenyl ring A with $R^3$]$-Y-CO-Y'-$[phenyl with R]

| No. | R¹ | R² | R³ | Q (pos.) | Y | Y' | R | IC₅₀ in μg/ml | LD₅₀ in mg/kg s.c. |
|---|---|---|---|---|---|---|---|---|---|
| 1 | —CH₃ | —CH₃ | H | —(CH₂)₄-(4) | — | — | H | 0.85 | >4000 |
| 2 | —CH₃ | —CH₃ | H | —(CH₂)₅-(4) | — | — | H | 0.16 | |
| 3 | —CH₃ | —CH₃ | H | —(CH₂)₆-(4) | — | — | H | 0.15 | |
| 4 | —CH₂CH₃ | —CH₂CH₃ | H | —(CH₂)₆-(3) | — | — | H | 0.60 | |
| 5 | —CH₃ | —CH₃ | H | —(CH₂)₆-(4) | — | —CH₂CH₂— | H | 0.60 | |
| 6 | —CH₂CH₃ | —CH₂CH₃ | H | —(CH₂)₆-(4) | — | —CH=CH— | H | 0.065 | |
| 7 | —CH₃ | —CH₃ | H | —(CH₂)₆-(4) | — | —CH₂— | H | 0.27 | |
| 8 | —CH₂CH₃ | —CH₂CH₃ | H | —(CH₂)₆-(4) | — | —CH₂CH₂— | H | 0.35 | |
| 9 | —CH₂CH₃ | —CH₂CH₃ | H | —(CH₂)₆-(4) | — | —CH₂CH₂— | H | 0.36 | |
| 10 | —CH₃ | —CH₃ | H | —(CH₂)₆-(3) | — | —CH=CH— | H | 2.30 | |
| 11 | —CH₃ | —CH₃ | H | —(CH₂)₆-(4) | — | —CH₂CH₂— | H | 1.00 | |
| 12 | —CH₃ | —CH₃ | H | —(CH₂)₆-(3) | — | — | 4-Fluoro | 0.18 | |
| 13 | —CH₂CH₃ | —CH₂CH₃ | H | —(CH₂)₆-(4) | — | — | H | 2.00 | |
| 14 | —CH₃ | —CH₃ | H | —(CH₂)₆-(3) | — | —C≡C— | H | 3.10 | |
| 15 | —CH₃ | —CH₃ | H | —(CH₂)₆-(4) | — | — | Pentafluoro | 0.89 | |
| 16 | —(CH₂)₂CH₃ | —(CH₂)₂CH₃ | H | —(CH₂)₆-(4) | — | — | H | 0.92 | |
| 17 | —(CH₂)₂CH₃ | | H | —(CH₂)₇-(4) | — | — | H | 0.60 | |
| 18 | —CH₃ | —(CH₂)₃— —CH₃ | H | —(CH₂)₈-(4) | — | — | H | 0.12 | |
| 19 | —CH₃ | —CH₃ | H | —(CH₂)₉-(4) | — | — | H | 0.42 | |
| 20 | —CH₃ | —CH₃ | H | —(CH₂)₁₀-(4) | — | — | H | 1.60 | |
| 21 | —CH₃ | —CH₃ | H | —(CH₂)₆-(4) | — | — | H | 2.00 | |
| 22 | —CH₃ | —(CH₂)₄— —CH₃ | H | —(CH₂)₆-(4) | — | — | H | 0.34 | |
| 23 | —CH₃ | —CH₃ | H | —(CH₂)₆-(4) | —CH₂— | — | H | 0.19 | |
| 24 | —CH₃ | H | H | —(CH₂)₆-(4) | — | — | H | 0.30 | |
| 25 | —CH₃ | —CH₃ | CH₃(3) | —(CH₂)₆-(4) | — | — | H | 0.19 | |
| 26 | —CH₃ | —CH₃ | H | —(CH₂)₆-(4) | — | — | 2,3-Dimethyl | 0.42 | |
| 27 | —CH₃ | —CH₃ | H | —(CH₂)₆-(4) | — | — | 2,4-Dichloro | 0.26 | |
| 28 | —CH₃ | —CH₃ | H | —(CH₂)₆-(4) | — | — | 3,5-Dichloro | 1.50 | |
| 29 | —CH₃ | —CH₃ | H | —(CH₂)₆-(4) | — | — | 4-Nitro | 0.28 | |
| 30 | —CH₃ | —CH₃ | Cl(3) | —(CH₂)₆-(4) | — | — | 2,4-Dichloro | 0.10 | |
| 31 | —CH₂—CH=CH₂ | —CH₃ | H | —(CH₂)₆-(4) | — | —CH₂— | H | 0.044 | 1000–2000 |
| 32 | —CH₂—CH=CH₂ | —CH₃ | H | —(CH₂)₆-(4) | — | — | H | 0.035 | |
| 33 | —CH₂—CH=CH₂ | —CH₃ | CH₃(3) | —(CH₂)₆-(4) | — | — | 4-Fluoro | 0.031 | |
| 34 | —CH₂—CH=CH₂ | —CH₃ | H | —(CH₂)₆-(4) | — | — | H | 0.032 | |
| 35 | —CH₂—CH=CH₂ | —CH₃ | H | —(CH₂)₆-(4) | — | — | 2,3-Dimethyl | 0.085 | |
| 36 | —CH₂—CH=CH₂ | —CH₃ | H | —(CH₂)₆-(4) | — | — | 2,4-Dichloro | 0.055 | |
| 37 | —CH₂—CH=CH₂ | —CH₃ | H | —(CH₂)₆-(4) | — | — | 3,5-Dichloro | 0.34 | |
| 38 | —CH₂—CH=CH₂ | —CH₃ | H | —(CH₂)₆-(4) | — | — | 4-Nitro | 0.04 | |
| 39 | —CH₂—CH=CH₂ | —CH₃ | Cl(3) | —(CH₂)₆-(4) | — | — | H | 0.025 | |
| 40 | —CH₂—CH=CH₂ | —CH₃ | Cl(3) | —(CH₂)₆-(4) | — | — | 2,4-Dichloro | 0.026 | |
| 41 | —CH₂—CH=CH—CH₂ | | H | —CH₂—CH=CH—CH₂-(4) | — | — | H | 0.02 | |
| 42 | —CH₂—CH=CH—CH₂ | | H | —CH₂—CH=CH—CH₂-(4) | — | — | 2,4-Dichloro | 0.007 | |
| 43 | —CH₃ | —CH₃ | H | —CH₂—CH=CH—CH₂-(4) | — | — | H | 0.22 | |
| 44 | —CH₃ | —CH₃ | H | —CH₂—CH=CH—CH₂-(4) | — | — | 2,4-Dichloro | 0.065 | |

The already mentioned synergistic activity of the compounds of formula I and of their pharmaceutically acceptable acid addition salts in combination with other sterol biosynthesis inhibitors such as ketoconazole and terbinafin can be demonstrated, for example, by means of the agar dilution method. For this purpose there are used casitone agar and inocula (10 cells/ml) of cultures of Candida albicans which are 48 hours old. The test substances (TS, compounds of formula I) are applied in concentrations of 80–1.25 μg/ml and the sterol biosynthesis inhibitors (SBI) are applied in concentrations of 20–0.001 μg/ml. with the dilution series being in each case 1:2. The cultures are incubated at 37° C. for 2 days. The minimum inhibitory concentrations (MIC) of the various active substances are then determined in the case of the application alone and in the case of the combined application and the fractional inhibitory concentration (FIC) is calculated according to the following formula from the MIC values determined:

$$FIC = \frac{MIC\ (TS\ \text{alone})}{MIC\ (TS\ \text{in combination})} + \frac{MIC\ (SBI\ \text{alone})}{MIC\ (SBI\ \text{in combination})}$$

A synergistic activity is present when the FIC is <0.5. The data contained in Table II hereinafter for compound 6 (according to Table I), a representative member of the class of compound defined by formula I, in combination with ketoconazole and respectively, terbinafin, representative sterol biosynthesis inhibitors, confirm the synergistic activity.

TABLE II

| | MIC in μg/ml | | | | |
|---|---|---|---|---|---|
| C. albicans | Compound 6 Ketoconazole alone | | Compound 6 Ketoconazole in combination | | FIC |
| $H_{12}$ | 40 | 5 | | 0.155 | 0.062 |
| $H_{29}$ | 40 | 0.25 | 10 | 0.03 | 0.375 |
| $H_{42}$ | 40 | 10 | 0.6 | 0.155 | 0.032 |
| $B_5$ | 40 | 5 | 10 | 0.31 | 0.125 |
| $B_4$ | 40 | 5 | 1.25 | 0.155 | 0.062 |
| | MIC in μg/ml | | | | |
| C. albicans | Compound 6 Terbinafin alone | | Compound 6 Terbinafin in combination | | FIC |
| $H_{12}$ | 40 | 100 | 2.5 | 6.25 | 0.125 |
| $H_{29}$ | 40 | 6.25 | 10 | 1.55 | 0.5 |
| $H_{42}$ | 40 | 100 | 2.5 | 6.25 | 0.125 |
| $B_5$ | 40 | 6.25 | 5 | 0.75 | 0.25 |
| $B_4$ | 40 | 12.5 | 5 | 0.55 | 0.25 |

The compounds of formula I and their pharmaceutically acceptable acid additions salts can be used as medicaments in mammals, human or non-human, for example, in unit dosage forms of pharmaceutical preparations for enteral, parenteral or topical application. They can be administered, for example, perorally, for example, in the form of tablets, coated tablets, dragees, hard and soft gelatine capsules, solutions, emulsions or suspensions, rectally, for example, in the form of suppositories, parenterally, for example, in the form of injection solutions or infusion solutions, or topically, for example, in the form of salves, creams or oils.

The manufacture of the pharmaceutical preparations can be effected in a manner familiar to any person skilled in the art by bringing the described compounds of formula I and their pharmaceutically acceptable acid addition salts, optionally in combination with other therapeutically valuable substances, for example the mentioned sterol biosynthesis inhibitors, into a galenical dosage form together with suitable, non-toxic, inert, therapeutically compatible solid or liquid carrier materials and, if desired, the usual pharmaceutical adjuvants.

Suitable carrier materials are not only inorganic carrier materials, but also organic carrier materials. Thus, lactose, maize starch or derivatives thereof, talc, stearic acid or its salts can be used, for example, as carrier materials for unit dosage forms such as tablets, coated tablets, dragees and hard gelatine capsules. Suitable carrier materials for soft gelatine capsules are, for example, vegetable oils, waxes, fats and semi-solid and liquid polyols (depending on the nature of the active substance no carriers are, however, required in the case of soft gelatine capsules). Suitable carrier materials for the manufacture of solutions and syrups are, for example, water, polyols, saccharose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

The usual stabilizing, preserving, wetting and emulsifying agents, consistency-improving agents, flavour-improving agents, salts for varying the osmotic pressure, buffer substances, solubilizers, coloring and coating agents and antioxidants come into consideration as pharmaceutical adjuvants.

The dosage of the compounds of formula I can vary within wide limits depending on the pathogenic fungi to be controlled, the age and the individual condition of the patient and on the mode of application and will, of course, be fitted to the individual requirements in each particular case. In the case of adult patients a daily dosage of about 0.01 to about 4 g, especially about 0.05 g to about 2 g, comes into consideration in monotherapy for the prevention and control of topical and systemic infections by pathogenic fungi. Depending on the dosage it is convenient to administer the daily dosage in several dosage units. In the case of combination therapy a daily dosage of about 0.01 g to about 2 g. especially about 0.02 g to about 1 g, of a compound of formula I and of about 0.02 g to about 0.2 g of a sterol biosynthesis inhibitor comes into consideration.

The pharmaceutical mono-preparations conveniently contain about 10 to about 1000 mg. preferably 50 to about 500 mg, of a compound of formula I The combination preparations conveniently contain about 10 to about 500 mg, preferably 20 to about 250 mg, of a compound of formula I and about 50 to about 100 mg of a sterol biosynthesis inhibitor.

The following Examples serve to illustrate the present invention in more detail. They are, however, not intended to limit its scope in any manner. The Examples 1 to 25 were actually conducted as set forth below. All temperatures are given in degrees Celsius. All ratios are at volume/volume unless otherwise stated.

EXAMPLE 1 a) A mixture of 2.5 g of N,N-dimethyl-6-amino-1-hexanol (Bull. Soc. Chim. France 1975, 2315), 3.4 g of 4-hydroxybenzophenone (Beilstein 8 (III), 1263), 4.5 g of triphenylphosphine and 140 ml of tetrahydrofuran was treated slowly at 20° with a solution of 2.7 ml of diethyl azodicarboxylate in 15 ml of tetrahydrofuran. After the dropwise addition the mixture was stirred at room temperature for a further 1 hour. The reaction mixture was evaporated in a rotary evaporator and the residue was chromatographed on 400 g of neutral aluminium oxide (activity grade III) with hexane:ethyl acetate (7:3). The yellowish oil obtained was dissolved in 25 ml of ether, whereupon the solution was treated with 25 ml of a 10 percent solution of hydrogen chloride in ether. The colorless crystals which separate were filtered off under suction, washed with ether and recrystallized from acetone. There were obtained 1.93 g (31%) of 4-[(6-dimethylamino)hexyl)oxy]benzophenone hydrochloride of m.p. 121°.

In an analogous manner, b) from N,N-dimethyl-6-amino-1-hexanol and 4'-hydroxychalcone (planta Med. 53, 110 1987)) there was obtained (E)-4'-[[6-(dimethylamino)hexyl]oxy]-3-phenylacrylophenone as a colorless solid of m.p. 43°-46° (yield 27%);

c) from N,N-dimethyl-6-amino-1-hexanol and 4'-hydroxy-3-phenylpropiophenone there was obtained 4'-[[6-(dimethylamino)hexyl]oxy]-3-phenylpropiophenone as a light yellowish solid of m.p. 27°-28° (yield 47%);

d) from N,N-dimethyl-6-amino-1-hexanol and 4-fluoro-4'-hydroxybenzophenone (European patent publication Nos. 167240 and 128692) there was obtained 4-[[6-(dimethylamino)hexyl]oxy]-4'-fluorobenzophenone as a colorless solid of m.p. 37°-38° (yield 52%);

e) from N,N-dimethyl-6-amino-1-hexanol and 2-(4-hydroxyphenyl)acetophenone (Indian J. pharmacol. 31,49 (1969)) there was obtained 2-[4-[[6-(dimethylamino)hexyl]oxy]phenyl]acetophenone of m.p 53°-54° (yield 30%);

f) from 6-(diethylamino)-1-hexanol (J. Chem. Soc. 1942, 428) and 4-hydroxybenzophenone there was obtained 4'-[[6-(diethylamino)hexyl]oxy]benzophenone as a yellowish oil (yield 30%);

g) from 6-(diethylamino)-1-hexanol and 3'-hydroxychalcone (Berichte 32, 1924 (1899)) there was obtained (E)-3'-[[6-(dimethylamino)hexyl]oxy]-3-phenylacrylophenone as a yellow oil (yield 38%);

h) from 1-oxo-3-phenyl-1-[4-hydroxyphenyl]propane (Chem. Zentralblatt II. 1949 (1927)) and 6-(dimethylamino)-1-hexanol there was obtained 3'-[[6-(dimethylamino)hexyl]]-oxy]-3-phenylpropiophenone as a yellowish oil (yield 42%);

i) from 4-hydroxy-2-phenylacetophenone (J. Org. Chem. 45, 1596 (1980)) and N,N-dimethyl-6-amino-1-hexanol there was obtained 4-[(6-dimethylamino)hexyl)oxy]-2-phenylacetophenone as a colorless solid of m.p. 69°-71° (yield 25%):

j) from 3-hydroxybenzophenone (Beilstein 8 (III). 1262) and N,N-dimethyl-6-amino-1-hexanol there was obtained 3-[(6-(dimethylamino)hexyl)oxy]benzophenone as a yellowish oil (yield 73%).

EXAMPLE 2 a) 100 ml of a 10 percent aqueous sodium hydroxide solution were added to a solution of 34.5 g of 1.5-dibromopentane, 9.9 g of 4-hydroxybenzophenone and 1.6 g of tetrabutylammonium bromide in 100 ml of methylene chloride. The heterogeneous mixture was stirred at room temperature overnight. The organic phase was separated, dried over sodium sulphate and evaporated. By chromatography of the residue on silica gel with hexane:ethyl acetate 7:3) there were obtained 13.47 g (78%) of 4-[(5-bromopentyl)oxy]benzophenone as a colorless oil.

A solution of 3.0 g of 4-[(5-bromopentyl)oxy]benzophenone in 30 ml of ethanol was heated to 90° in a pressure tube for 1.5 hours with 16 ml of a 33 percent solution of dimethylamine in ethanol. After cooling the mixture was poured into water and extracted three times with ethyl acetate. The organic phases, dried over sodium sulphate, were evaporated and the residue was chromatographed on neutral aluminium oxide (activity grade III) with hexane:ethyl acetate 7:3). There were obtained 2.69 g (97%) of 4- (5-(dimethylamino)pentyl)oxy]benzophenone as a colorless oil.

$^1$H—NMR (CDC$_{13}$): 1.6–2.0 (m,6H); 2.23 (s,6H); 2.30 (t,J=7Hz,2H); 4.05 (t,J=7Hz 2H); 6.95 (d,J=9Hz,2H); 7.3–7.9 m,4H); 7.83 (d,J=9Hz,2H) ppm.

In an analogous manner, b) from 1,8-dibromooctane and 4-hydroxybenzophenone there was obtained 4-[(8-bromooctyl)oxy]benzophenone as colorless crystals of m.p. 59°-61° (yield 81%) and therefrom with dimethylamine there was obtained 4-[(8-dimethylamino)octyl)oxy]benzophenone as a yellowish oil (yield 42%).

$^1$H—NMR (CDCl$_3$): 1.3–1.6 (m,10H): 1.80 (qui,J=7Hz,2H): 2.22 (s,6H); 2.25 (t,J=7Hz,2H); 4.03 (t,J=7Hz,2H): 6.94 (d,J=9Hz,2H): 7.4–7.65 (m,3H): 7.7–7.9 (m,4H) ppm;

c) from 1,6-dibromohexane and 4-hydroxybenzophenone there was obtained 4-[(6-bromohexyl)oxy]benzophenone as colorless crystals of m.p. 47°-49° (yield 77%) and therefrom with pyrrolidine there was obtained 4-[(6-(pyrrolidino)hexyl)oxy]benzophenone as a colorless oil (yield 33%).

$^1$H—NMR (CDCl$_3$): 1.3–2.0 (m,12H); 2.3–2.65 (m,6H); 4.05 (t,J=7Hz,2H); 6.97 (d,J=9Hz,2H); 7.45–8.0 (m,7H) ppm;

d) from 1,4-dibromobutane and 4-hydroxybenzophenone there was obtained 4-[(4-bromobutyl)oxy]benzophenone (yield 86%) and therefrom with dimethylamine there was obtained 4-[[4-(dimethylamino)butyl]oxy]benzophenone as a yellowish oil (yield 80%);

e) from 1,6-dibromohexane and 4-hydroxybenzophenone there was obtained 4-[(6-bromohexyl)oxy]benzophenone (yield 66%) and therefrom with N,N-dipropylamine there was obtained 4-[[6-(dipropylamino)hexyl]oxy]benzophenone as a yellowish oil (yield 94%);

f) from 4-[(6-bromohexyl)oxy]benzophenone and trimethylene imine there was obtained 4-[(6-(azetidinyl)hexyl)oxy]benzophenone as a yellowish oil (yield 5%);

g) from 1,7-dibromoheptane and 4-hydroxybenzophenone there was obtained 4-[(7-bromoheptyl)oxy]benzophenone (yield 82%) and therefrom with dimethylamine there was obtained 4-[[7-(dimethylamino)heptyl]oxy]benzophenone as a Yellowish oil (yield 90%).

h) from 1.9-dibromononane and 4-hydroxybenzophenone there was obtained 4-[(9-bromononyl)oxy]benzophenone (yield 74%) and therefrom with dimethylamine there was obtained 4-[[9-(dimethylamino)nonyl]oxy]benzophenone as a colorless solid with a m.p. of 44°-45° (yield 77%);

i) from 1,10-dibromodecane and 4-hydroxybenzophenone there was obtained 4-[(10-bromodecyl)oxy]benzophenone (yield 75%) and therefrom with dimethylamine there was obtained 4-[[10-(dimethylamino)decyl]oxy]benzophenone of m.p. 33°-35° (yield 90%);

j) from 4-[[6-bromohexyl)oxy]benzophenone and methylamine there was obtained 4- [6-(methylamino)hexyl]oxy]benzophenone. By treatment with ethereal hydrochloric acid there was obtained the corresponding hydrochloride in a yield of 13%; m.p. 155°-157°;

k) from 4-[(6-bromohexyl)oxy]benzophenone and N-allyl-methylamine there was obtained 4-[[6-(allylmethylamino)hexyl]oxy]benzophenone as a yellowish oil (yield 55%);

l) from 1,6-dibromohexane and 4-hydroxy-2-phenylacetophenone there was obtained 4-[(6-bromohexyl)oxy]-2-phenylacetophenone as a yellowish solid with a m.p. of 75°-78° (yield 71%) and therefrom with N-allyl-methylamine there was obtained 4-[[6-(allylmethylamino)hexyl]oxy]-2-phenylacetophenone as a yellowish oil (yield 48%);

m) from 4-fluoro-4'-hydroxybenzophenone (European Patent Publication Nos. 167240 and 128692) and 1,6-dibromohexane there was obtained 4-[(6-bromohexyl)oxy]-4'-fluorobenzophenone as colorless crystals with a m.p. of 79° (yield 57%) and therefrom with N-allyl-methylamine there was obtained 4-[[6-(allylmethylamino)hexyl]oxy]-4'-fluorobenzophenone, which was converted into the hydrochloride (yield 74%), m.p. 84°;

n) from trans-1,4-dibromobutene and 4-hydroxybenzophenone there was obtained 4-[(4-bromo-2-butenyl-)oxy]benzophenone as a colorless solid with a m.p. of 100° (yield 45%) and therefrom with dimethylamine there was obtained trans-4-[[4-(dimethylamino)-2-butenyl]oxy]benzophenone as a colorless solid with a m.p. of 48°-50° (yield 69%);

o) from 4-[(4-bromo-2-butenyl)oxy]benzophenone and N-allyl-methylamine there was obtained trans-4-[[4-(allylmethylamino)-2-butenyl]oxy]benzophenone, which was converted into the hydrochloride (yield 88%), m.p. 90°-91°.

EXAMPLE 3 a) A mixture of 2.17 g of 6-diethylamino-1-hexanol (J. Chem. Soc. 1942, 428), 1.52 g of 4-hydroxy-benzaldehyde and 3.3 g of triphenylphosphine in 100 ml of tetrahydrofuran was treated slowly at 20° with a solution of 1.97 g of diethyl azodicarboxylate. After the dropwise addition the mixture was stirred at room temperature for a further 5 hours. The reaction mixture was then evaporated in a rotary evaporator. The residue was chromatographed on 400 g of neutral aluminium oxide (activity grade III) with hexane:ethyl acetate 7:3). There were obtained 2.22 g (64%) of 4- [[6-(diethylamino)hexyl]oxy]benzaldehyde as a yellowish oil.

b) A solution of 4-[[6-(diethylamino)hexyl]oxy] benzaldelyde from Example 3a) in 20 ml of ether was added dropwise at 0° under argon to a solution of phenethylmagnesium bromide (from 1.47 g of phenethyl bromide and 143 mg of magnesium in 20 ml of ether). The reaction mixture was stirred at room temperature for 3 hours, then poured into 100 ml of saturated ammonium chloride solution and extracted three times with 100 ml of dichloromethane each time. The organic phases were dried over magnesium sulphate and evaporated. The crude 1-[4-[[6-(diethylamino)hexyl]oxy]phenyl]-3-phenylpropanol was used in the next step without further purification.

c) A solution of 1.58 ml of dimethyl sulphoxide in 10 ml of methylene chloride was added dropwise at −60° durinq 5 minutes to a solution of 0.8 ml of oxalyl chloride in 30 ml of methylene chloride. After stirring for 2 minutes a solution of the crude 1-[4-[[6-(diethylamino)-hexyl]oxy]phenyl]-3-phenylpropanol in 20 ml of methylene chloride was added thereto at −60° within 10 minutes. After 15 minutes 7.5 ml of triethylamine were added thereto at −60° and the reaction mixture was left to warm to room temperature. After one hour at room temperature 100 ml of water were added thereto, the organic phase was separated and the aqueous phase was extracted twice with 100 ml of methylene chloride each time. The combined organic phases were dried over magnesium sulphate and evaporated. After chromatography of the residue on 240 g of silica gel with ammonium hydroxide/methanol/methylene chloride (1:10:90) there were obtained 1.76 g (37%) of 4'-[[6-(diethylamino)hexyl oxy]-3-phenylpropiophenone as a yellow oil which crystallizes upon standing; m.p. 83°-84°.

In an analogous manner, d) from 3-[[6-(diethylamino)hexyl]oxy]benzaldehyde (prepared from 3-hydroxybenzaldehyde and 6-(diethylamino)-1-hexanol) and phenethylmagnesium bromide and oxidation of the condensation product with oxalyl chloride/dimethyl sulphoxide there was obtained 3'-[[6-(diethylamino)hexyl]oxy]-3-phenypropiophenone as a yellow oil (yield 38%);

e) from 3-[[6-(diethylamino)hexyl]oxy]benzaldehyde and lithium phenylacetylide there was obtained 3-[[6-(diethylamino)hexyl]oxy]-α-(phenylethynyl)benzyl alcohol and therefrom there was obtained 3'-[[6-(diethylamino)hexyl]oxy]-3-phenylpropiolophenone (yield 85%).

EXAMPLE 4 a) 20.75 ml of a 1.6M solution of n-butyllithium in hexane was added dropwise at −78° under argon to a solution of 5.52 g of pentafluorobenzene in 50 ml of tetrahydrofuran. The reaction mixture was stirred for 30 minutes at −78°. At the same temperature there was then added dropwise thereto a solution of 4.47 g of anisaldehyde in 25 ml of tetrahydrofuran. After 1 hour at −78° the mixture was left to warm to room temperature and was stirred for a further 1 hour. The reaction mixture was poured into 100 ml of a saturated ammonium chloride solution and extracted three times with 100 ml of ethyl acetate each time. The organic phases were washed with 100 ml of a saturated sodium chloride solution and dried over magnesium sulphate. After evaporation there were obtained 10 g of crude 2,3,4,5,6-pentafluorophenyl-4'-methoxyphenyl carbinol.

b) A solution of crude 2,3,4,5,6-pentafluorophenyl-4'-methoxyphenyl carbinol from Example 4a) in 60 ml of methylene chloride was added dropwise within 15 minutes at −78° under argon to a solution of 3.3 ml of oxalyl chloride and 5.6 ml of dimethyl sulphoxide in 130 ml of methylene chloride. The mixture was stirred at −78° for 15 minutes. 27.6 ml of triethylamine were then added dropwise at −78° within 15 minutes. The mixture was then left to warm to room temperature. The reaction mixture was treated with 500 ml of water. The organic phase was separated and the aqueous phase was extracted twice with 200 ml of methylene chloride each time. The combined organic phases were dried over magnesium sulphate and evaporated in a rotary evaporator. The residue was chromatographed on 920 g of silica gel with methylene chloride. There were obtained 7.82 g (78%) of 2,3,4,5,6-pentafluoro-4'-methoxy-benzophenone as a colorless oil.

c) A solution of 5.6 g of 2,3,4,5,6-pentafluoro-4'-methoxy-benzophenone in 100 ml of ethylene chloride was added dropwise at −7° under argon to a solution of 23.23 g of boron tribromide in 100 ml of ethylene chloride. The reaction mixture was warmed to room temperature and stirred at this temperature for 5 hours. The reaction mixture was poured into 200 ml of ice-cold water and extracted three times with 150 ml of methylene chloride each time. The combined extracts were washed with 200 ml of water and dried over magnesium sulphate. After evaporation of the solvent the residue was chromatographed on 900 g of silica gel with methylene chloride. There were obtained 3.87 g (72%) of 2,3,4,5,6-pentafluoro-4'-hydroxy-benzophenone; m.p. 138°–140°.

d) In analogy to Example 1,2,3,4,5,6-pentafluoro-4'-hydroxybenzophenone and 6-(dimethylamino)-1-hexanol there was obtained 4'-[[6-(dimethylamino)hexyl]oxy]-2,3,4,5,6-pentafluorobenzophenone as a colorless oil (yield 37%). $^1$H—NMR (CDCl$_3$): 1.3–1.9 (m,8H); 2.26 (s,6H); 2.1–2.3 (m,2H); 4.06 (t,J=7Hz,2H); 6.96 (d,J=9Hz,2H); 7.84 (d,J=9Hz,2H) ppm.

EXAMPLE 5 a) In analogy to Example 3b), from 4-[[6-(diethylamino)-hexyl]oxy]benzaldehyde and phenylacetylene/butyllithium there was obtained crude 4'-[[6-(diethylamino)hexyl]oxy]phenyl phenylethynyl carbinol (yield 50%).

b) A solution of 1.58 g of 4'-[[6-(diethylamino)hexyl]oxy]phenyl phenylethynyl carbinol in 60 ml of methylene chloride was treated with 2.07 g of activated manganese dioxide. After 20 hours the reaction mixture was filtered through siliceous earth. After evaporation of the filtrate the residue was chromatographed on 100 g of neutral aluminium oxide (activity grade III) with hexane:ethyl acetate (2:1). There were obtained 1.34 g (50%) of 4'-[[6-(diethylamino)hexyl]oxy]-3-phenyl-propiolophenone as a colorless oil.

EXAMPLE 6 a) A solution of 24 g of 2-methylanisole, 35 g of N-bromosuccinimide and 1.24 g of dibenzoyl peroxide in 150 ml of carbon tetrachloride was heated to boiling under reflux for 12 hours. After cooling the solution was filtered and the filtrate is evaporated. The residue was recrystallized from hexane. There were obtained 18.6 g (47%) of 4-bromo-2-methylanisole as a colorless solid; m.p. 66°–68°.

b) The corresponding Grignard reagent was prepared from 10 g of 4-bromo-2-methylanisole and 1.21 g of magnesium shavings in 30 ml of tetrahydrofuran and was added dropwise to a solution, pre-cooled to −72°, of 7 g of benzoyl chloride in 80 ml of tetrahydrofuran. In so doing, the temperature was held at below −65°. After the dropwise addition the mixture was stirred at 20° for 0.5 hour, whereupon it was hydrolyzed with 400 ml of ice-water. The solution, acidified with dilute hydrochloric acid, was extracted with ether and the organic phase was dried and evaporated. By chromatography of the residue on silica gel with hexane:ethyl acetate 7:3) there were obtained 6.17 g (55%) of 4-methoxy-3-methylbenzophenone as a yellowish oil.

c) A mixture of 6.17 g of 4-methoxy-3-methylbenzophenone. 65 ml of glacial acetic acid and 103 ml of a 62 percent hydrobromic acid solution is heated to boiling under reflux for 3 hours. The dark solution obtained is concentrated, extracted with ethyl acetate and the organic phase is dried and evaporated. The residue is chromatographed on silica gel with hexane:ethyl acetate (7:3). There are obtained 2.90 g (50%) of 3-methyl-4-hydroxybenzophenone as a yellowish solid with a m.p. of 170°–173°.

d) In analogy to Example 2, from 1,6-dibromohexane and 3-methyl-4-hydroxybenzophenone there was obtained 4-[(6-bromohexyl)oxy]-3-methylbenzophenone as a yellowish oil (yield 79%) and therefrom with dimethylamine there was obtained 4-[[6-(dimethylamino)hexyl]oxy]-3-methylbenzophenone, which was converted into the hydrochloride (yield 61%); m.p. 162°–163°.

EXAMPLE 7

In analogy to Example 2, from 4-[(6-bromohexyl)oxy]-3-methylbenzophenone and N-allyl-methylamine there was obtained 4-[[6-(allylmethylamino)hexyl]oxy]-3-methylbenzophenone, which was converted into the hydrochloride (yield 49%); m.p. 112°–113°.

EXAMPLE 8 a) From the Grignard reagent from 2-bromo-m-xylene and 4-methoxybenzoyl chloride there was obtained in analogy to Example 6b) 4-methoxy-2',3'-dimethylbenzophenone as a yellowish oil (yield 47%).

b) In analogy to Example 6c) there was obtained therefrom 4-hydroxy-2',3'-dimethylbenzophenone as yellowish crystals (yield 72%); m.p. 155°–158°.

c) In analogy to Example 2 there was obtained therefrom with 1,6-dibromohexane 4-[(6-bromohexyl)oxy]-2',3'-dimethylbenzophenone as a yellowish oil (yield 78%) and therefrom with dimethylamine there was obtained 4-[[6-(dimethylamino)hexyl]oxy]-2',3'-dimethylbenzophenone, which was converted into the hydrochloride (yield 81%); m.p. 117°–120°.

EXAMPLE 9

From 4-[(6-bromohexyl)oxy -2',3'-dimethylbenzophenone and N-allyl-methylamine there was obtained in analogy to Example 2,4-[[6-(allylmethylamino)hexyl]oxy]-2',3'-dimethylbenzophenone as a yellowish oil (yield 82%).

EXAMPLE 10 a) From the Grignard reagent from 4-bromoanisole and 2,4-dichlorobenzoyl chloride there was obtained in analogy to Example 6b) 2,4-dichloro-4'-methoxybenzophenone as a yellow oil (yield 76%).

b) In analogy to Example 6c) there was obtained therefrom 4-hydroxy-2',4'-dichlorobenzophenone as yellowish crystals (yield 63%): m.p. 140°.

c) In analogy to Example 2 there was obtained therefrom with 1,6-dibromohexane 4-[(6-bromohexyl)oxy]-2',4'-dichlorobenzophenone as a colorless oil (yield 86%) and therefrom with N-allyl-methylamine there was obtained 4-[[6-(allylmethylamino)hexyl]oxy]-2',4'-dichlorobenzophenone as a yellowish oil (yield 67%)

EXAMPLE 11

From 4-hydroxy-2',4'-dichlorobenzophenone and N,N-dimethyl-6-amino-1-hexanol there was obtained in analogy to Example 1, 4-[[6-(dimethylamino)hexyl]oxy]-2',4'-dichlorobenzophenone as a colorless oil (yield 31%).

EXAMPLE 12

From the Grignard compound from 4-bromoanisole and 3,5-dichlorobenzoyl chloride there was obtained in analogy to Example 6b) 3,5-dichloro-4'-methoxybenzophenone as a colorless solid (yield 37%).

In analogy to Example 6c) there was obtained therefrom 4-hydroxy-3',5'-dichlorobenzophenone as brownish crystals (yield 91%); m.p. 183°.

In analogy to Example 2 there is obtained therefrom with 1.6-dibromohexane 4-[(6-bromohexyl)oxy]-3',5'-dichlorobenzophenone as a colorless solid (yield 49%) with a m p of 70° and therefrom with dimethylamine there was obtained 4-[[6-(dimethylamino)hexyl]oxy]-3',5'-dichlorobenzophenone, which was converted into the hydrochloride (yield 66%); m.p 148°-149°.

EXAMPLE 13

From 4-[(6-bromohexyl)oxy]-3',5'-dichlorobenzophenone and N-allyl-methylamine there was obtained in analogy to Example 2 4-[[6-(allylmethylamino)hexyl]oxy]-3',5'-dichlorobenzophenone, which was converted into the hydrochloride (yield 74%); m.p. 111°-112°.

EXAMPLE 14

From 4-hydroxy-2',4'-dichlorobenzophenone and trans-1,4-dibromobutene there was obtained in analogy to Example 2. 4-[(4-bromo-2-butenyl)oxy]-2',4'-dichlorobenzophenone as a sticky resin (yield 73%) and therefrom with dimethylamine there was obtained trans-4-[[4-(dimethylamino)-2-butenyl]oxy]-2',4'-dichlorobenzophenone, which was converted into the hydrochloride (yield 82%); m.p. 147°.

EXAMPLE 15

From 4-[(4-bromo-2-butenyl)oxy]-2',4'-dichlorobenzophenone and N-allyl-methylamine there was obtained in analogy to Example 2, trans-4-[[4-(allylmethylamino)-2-butenyl]oxy]-2',4'-dichlorobenzophenone, which was converted into the hydrochloride (yield 80% ; m.p. 98°.

EXAMPLE 16 a) 150 ml of nitrobenzene were cooled in an ice-bath and treated portionwise with 41 g of aluminium chloride. In so doing, the temperature was held at below 5°. Subsequently, a solution of 50 g of 4-nitrobenzoyl chloride in 50 ml of nitrobenzene was added dropwise in such a manner that the temperature remains at below 5°. At the same temperature there were added dropwise 27.8 g of anisole. Subsequently, the mixture was stirred at 20° overnight. The solution was poured on to 1 liter of ice-water, extracted with methylene chloride, dried over magnesium sulphate and concentrated. The nitrobenzene was distilled off in a high vacuum and the yellowish crystals which remained were recrystallized from cyclohexane. There were obtained 36.5 g (52%) of 4-methoxy-4'-nitrobenzophenone as a yellow solid; m.p. 124°.

b) From 4-methoxy-4'-nitrobenzophenone and hydrobromic acid there was obtained in analogy to Example 6c) 4-hydroxy-4'-nitrobenzophenone as yellow crystals (yield 75%); m.p. 196°.

c) In analogy to Example 2, from 4-hydroxy-4'-nitrobenzophenone and 1,6-dibromohexane there was obtained 4-[(6-bromohexyl)oxy]-4'-nitrobenzophenone as a yellow solid with a m.p. of 61° (yield 65% and therefrom with dimethylamine there was obtained 4-[[6-(dimethylamino)hexyl]oxy]-4'-nitrobenzophenone, which was converted into the hydrochloride (yield 80%); m.p. 101°.

EXAMPLE 17

From 4-[(6-bromohexyl)oxy]-4'-nitrobenzophenone and N-allyl-methylamine there was obtained in analogy to Example 2 4-[[6-(allylmethylamino)hexyl]oxy]-4'-nitrobenzophenone, which was converted into the hydrochloride (yield 85%); m.p. 79°.

EXAMPLE 18 a) From 2-chloroanisole and benzoyl chloride there was obtained in analogy to Example 16a) 3-chloro-4-methoxybenzophenone as a colorless solid (yield 72%); m.p. 87°.

b) In analogy to Example 6c) there was obtained therefrom 3-chloro-4-hydroxybenzophenone as a yellowish solid (yield 91%); m.p. 180°.

c) In analogy to Example 2 there was obtained therefrom with 1,6-dibromohexane 4-[(6-bromohexyl ]-3-chlorobenzophenone as a colorless solid with a m.p. of 58° (yield 68%) and therefrom with dimethylamine there was obtained 4-[[6-(dimethylamino)hexyl]oxy]-3-chlorobenzophenone, which was converted into the hydrochloride (yield 94%); m.p. 195°.

EXAMPLE 19

From 4-[(6-bromohexyl)oxy]-3-chlorobenzophenone and N-allyl-methylamine there was obtained in analogy to Example 2 4-[[6-(allylmethylamino)hexyl]oxy]-3-chlorobenzophenone, which was converted into the hydrochloride (Yield 98%); m.p. 133°.

EXAMPLE 20 a) From 2-chloroanisole and 2,4-dichlorobenzoyl chloride there was obtained in analogy to Example 16a) 2',3,4'-trichloro-4-methoxybenzophenone as yellowish crystals (yield 87%); m.p. 98°.

b) Therefrom there was obtained in analogy to Example 6c) 2',3,4'-trichloro-4-hydroxybenzophenone as yellowish crystals (yield 89%); m.p. 145°.

In analogy to Example 2 there was obtained therefrom with 1,6-dibromohexane, 4-[(6-bromohexyl)oxy]-2',3,4'-trichlorobenzophenone as a yellowish oil (yield 21%) and therefrom with dimethylamine there was obtained 4-[[6-(dimethylamino)hexyl]oxy]-2',3,4'-trichlorobenzophenone, which was converted into the hydrochloride (yield 49%); m.p. 91°.

EXAMPLE 21

From 4-[(6-bromohexyl)oxy]-2',3,4'-trichlorobenzophenone and N-allyl-methylamine there was obtained in analogy to Example 2, 4-[[6-(allylmethylamino)hexyl]oxy]-2',3,4'-trichlorobenzophenone, which was converted into the hydrochloride (yield 38%); m. p. 100°.

EXAMPLE 22

In analogy to Example 2, from 4-hydroxy-4'-nitrobenzophenone and trans-1,4-dibromobutene there was obtained 4-[(4-bromo-2-butenyl)oxy]-4'-nitrobenzophenone as a yellowish solid [yield 71%]and therefrom with dimethylamine there was obtained trans-4-[[4-(dimethylamino)-2-butenyl]oxy]-4'-nitrobenzophenone, which was converted into the hydrochloride (yield 90%); m.p. 144°.

EXAMPLE 23

From 4-[(4-bromo-2-butenyl)oxy]-4'-nitrobenzophenone and N-allyl-methylamine there was obtained in analogy to Example 2, trans-4-[[4-(allylmethylamino)-2- butenyl]oxy]-4,-nitrobenzophenone, which was converted into the hydrochloride (yield 85%); m.p. 152°.

EXAMPLE 24 a) From 4-bromobenzoyl chloride and anisole there was obtained in analogy to Example 16a) 4-bromo-4'-methoxybenzophenone as a colorless solid (yield 65%).

b) Therefrom there was obtained in analogy to Example 6c) 4-bromo-4'-hydroxybenzophenone as a yellowish solid (yield 77%).

c) In analogy to Example 2 there was obtained therefrom with trans-1,4-dibromobutene 4-[(4-bromo-2-butenyl)oxy]-4'-bromobenzophenone as colorless crystals [yield 64%] and therefrom with dimethylamine there was obtained trans-4-[[4-(dimethylamino)-2-butenyl]oxy]-4'-bromobenzophenone, which was converted into the hydrochloride (yield 85%); m.p. 184°-185°.

EXAMPLE 25

From 4-[(4-bromo-2-butenyl)oxy]-4'-bromobenzophenone and N-allyl-methylamine there was obtained in analogy to Example 2 trans-4-[[4-(allylmethylamino)-2-butenyl]oxy]-4'-bromobenzophenone, which was converted into the hydrochloride (yield 83%); m.p. 116°-117°.

EXAMPLE A

The compound 4-[(6-(dimethylamino)hexyl)oxy]-2-phenylacetophenone can be used as follows as the active ingredient for the manufacture of tablets:

| Ingredients | mg/tablet |
|---|---|
| Active ingredient | 200 |
| Powd. lactose | 100 |
| Povidone K 30 | 15 |
| Na carboxymethylstarch | 10 |
| Talc | 3 |
| Magnesium stearate | 2 |
| Tablet weight | 330 |

The active ingredient and the powd. lactose are mixed intensively. The mixture obtained is then moistened with an aqueous solution of povidone K 30 and kneaded, whereupon the mass obtained is granulated, dried and sieved. The granulate is mixed with the remaining ingredients and then pressed to tablets of suitable size.

We claim:

1. A method for treating a mammal having an infection caused by pathogenic fungi, which comprises administering to said mammal a compound having the formula

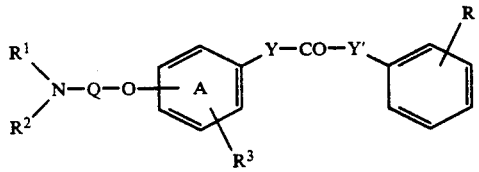

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 4 to 11 carbon atoms and at least 4 carbon atoms between the two free valencies or alkenylene with 4 to 11 carbon atoms and at least 4 carbon atoms between the two free valencies and each of Y and Y' individually a direct bond or the group $-CH_2-$, $-CH_2CH_2-$, $-CH=CH-$ or $-C\equiv C-$, the group $R^1R^2N-Q-O-$ is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy, or a pharmaceutically acceptable acid addition salt thereof, in an amount which is effective in treating an infection caused by pathogenic fungi.

2. The method of claim 1 wherein the compound has the formula

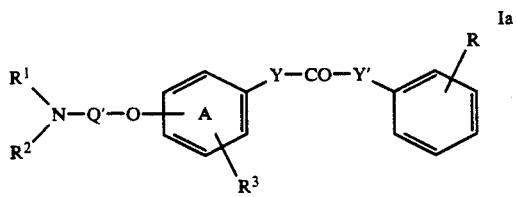

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 5 to 11 carbon atoms and at least 5 carbon atoms between the two free valencies or alkenylene with 4 to 11 carbon atoms and at least 4 carbon atoms between the two free valencies and each of Y and Y' individually is a direct bond or the group $-CH_2-$, $-CH_2CH_2-$, $-CH=CH-$ or $-C\equiv C-$, the group $R^1R^2N-Q-O-$ is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy.

3. The method of claim 1 wherein said compound of formula I is 4-[(4-(dimethylamino)butyl)oxy]benzophenone.

4. A method of prophylaxis against the development of infections caused by pathogenic fungi, which comprises administering to mammals susceptible to such infections a compound of formula

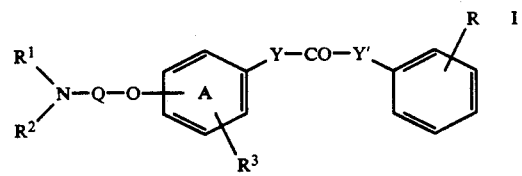

wherein each of $R^1$ and $R^2$ individually is hydrogen, lower alkyl or lower alkenyl or together are straight-chain alkylene with 2 to 4 carbon atoms, $R^3$ is hydrogen, halogen, or lower alkyl, Q is alkylene with 4 to 11 carbon atoms and at least 4 carbon atoms between the two free valencies or alkenylene with 4 to 11 carbon atoms and at least 4 carbon atoms between the two free valencies and each of Y and Y' individually is a direct bond or the group $-CH_2-$, $-CH_2CH_2-$, $-CH=CH-$ or $-C\equiv C-$, the group $R^1R^2N-Q-O-$ is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy, or a pharmaceutically acceptable acid addition salt thereof, in an amount which is effective as a prophylaxis for pathogenic fungi.

5. The method of claim 4 wherein the compound has the formula

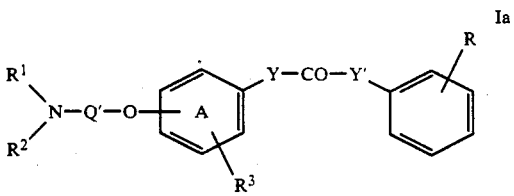

wherein each of $R^1$ and $R^2$ individually is hydrogen, lower alkyl or lower alkenyl or together are straight-chain alkylene with 2 to 4 carbon atoms, $R^3$ is hydrogen, halogen or lower alkyl, Q is alkylene with 5 to 11 carbon atoms and at least 5 carbon atoms between the two free valencies or alkenylene with 4 to 11 carbon atoms and at least 4 carbon atoms between the two free valencies and each of Y and Y' individually is a direct bond or the group —$CH_2$—, —$CH_2CH_2$—, —CH=CH— or —C≡C—, the group $R^1R^2N$—Q—O— is attached to the 3- or 4-position of ring A and the symbol R designates that the ring to which it is attached is unsubstituted or is substituted with at least one substituent selected from the group consisting of halogen, trifluoromethyl, cyano, nitro, lower alkyl and lower alkoxy.

* * * * *